(12) United States Patent
Ooike et al.

(10) Patent No.: US 6,451,192 B1
(45) Date of Patent: Sep. 17, 2002

(54) SIMPLIFIED ELECTROPHORESIS APPARATUS

(75) Inventors: Akio Ooike, Komoro; Kouichi Kudo, Saku; Eizo Sugimoto, Tokyo; Masato Murakami, Kashiwa; Hiromu Ishibashi, Tokyo, all of (JP)

(73) Assignees: Cosmo Bio Co., Ltd. (JP); Advance Co., Ltd. (JP)

(*) Notice: Subject to any disclaimer, the term of this patent is extended or adjusted under 35 U.S.C. 154(b) by 0 days.

(21) Appl. No.: 09/513,314

(22) Filed: Feb. 25, 2000

Related U.S. Application Data (63) Continuation-in-part of application No. 08/871,228, filed on Jun. 9, 1997, now abandoned.

(30) Foreign Application Priority Data

Jul. 18, 1996 (JP) .............................. 8-206409

(51) Int. Cl.⁷ .......................... G01N 27/27; C02F 1/40; B01D 57/02; C25B 15/00
(52) U.S. Cl. ...................... 204/600; 204/606; 204/607; 204/616; 204/618; 204/456; 204/457; 204/466; 204/467
(58) Field of Search ................. 204/456–470, 204/606–624

(56) References Cited

U.S. PATENT DOCUMENTS

| | | | | |
|---|---|---|---|---|
| 3,856,656 A | * | 12/1974 | Brink | 204/299 |
| 4,608,146 A | * | 8/1986 | Penaluna | 204/299 |
| 4,773,984 A | * | 9/1988 | Flesher et al. | 204/618 |
| 4,975,174 A | * | 12/1990 | Bambeck et al. | 204/618 |
| 5,055,172 A | * | 10/1991 | Cathel et al. | 204/607 |
| 5,112,470 A | * | 5/1992 | Sylvester | 204/618 |
| 5,242,568 A | * | 9/1993 | Ehr et al. | 204/607 |
| 5,405,520 A | * | 4/1995 | Helfer | 204/606 |
| 5,407,552 A | * | 4/1995 | Lebacq | 204/619 |
| 5,415,758 A | * | 5/1995 | Comeau | 204/299 |
| 5,460,709 A | * | 10/1995 | Sarrine et al. | 204/299 |
| 5,516,402 A | * | 5/1996 | Sarrine et al. | 204/461 |
| 5,582,702 A | * | 12/1996 | Cabilly et al. | 204/456 |
| 5,779,869 A | * | 7/1998 | Helfer et al. | 204/456 |
| 5,792,332 A | * | 8/1998 | Montecino et al. | 204/467 |
| 5,846,395 A | * | 12/1998 | Sarrine et al. | 204/456 |
| 5,904,825 A | * | 5/1999 | Axelsson et al. | 204/616 |

\* cited by examiner

*Primary Examiner*—Jill Warden
*Assistant Examiner*—Jennine Brown
(74) *Attorney, Agent, or Firm*—McGlew and Tuttle, P.C.

(57) ABSTRACT

The electrophoresis apparatus comprises rectifier (A) which rectifies an AC current from a universal AC power source and outputs a rectified wave, an electrophoresis cell and an electric controller which applies an electric output from the rectifier (A) to a carrier disposed in the electrophoresis cell, the elastic controller comprising a controller (3) for indirectly controlling, in accordance with external inputs, a driving section (6) which controls an electric output from the rectifier circuit. The electrophoresis cell unit defines a recess for receiving the electric controller, and a cover is positionable over the electrophoresis cell unit. The cover includes a cover terminal, where the cover and cover terminal are shaped to electrically connect an output terminal of the electric controller to an input terminal of the electrophoresis cell unit when the; cell covers the electrophoresis cell unit.

13 Claims, 6 Drawing Sheets

SIMPLIFIED ELECTROPHORESIS APPARATUS

This is a continuation-in-part of application Ser. No. 08/871,228 filed Jun. 9, 1997, and now abandoned and the entire disclosure of this prior application is considered to be part of the disclosure of the accompanying application and is hereby incorporated by reference therein.

FIELD OF THE INVENTION

The present invention relates to a simplified electrophoresis apparatus which is used for fixing, retrieving and refining samples extracted from living bodies in analyses of DNA and proteins by electrophoresis which is widely utilized as a basic technique for molecular biology, biochemistry and clinical chemistry

BACKGROUND OF THE INVENTION

An electrophoresis apparatus, disclosed by Japanese Utility Model Application Laid-Open No. 63-39639, is known as a conventional simplified electrophoresis apparatus. This electrophoresis apparatus is composed only of fuses, rectifier means and switches which are used for starting and stopping operations and changing output waveforms. This electrophoresis apparatus is capable of supplying an electric current in accordance with an impedance of an electrophoresis carrier.

However, the electrophoresis apparatus disclosed by the invention mentioned above is connected directly to a universal AC power source such as a domestic AC 100 V power source and may possibly allow a large capacity electric current to be supplied when impedance of an electrophoresis carrier is abruptly lowered or a member of the electrophoresis apparatus is shorted.

Even though such a large capacity electric current is very hazardous to human bodies, the prior art electrophoresis apparatus provides electric insulation only by breakage of built-in fuses and a protective casing casing which accommodates the electronic circuits. Accordingly, users must always pay attentions to deterioration of the mechanical structure of the switching means caused due to frequent operations, long term use and/or adhesion of splashed electrophoretic gels to the operating switches. Furthermore, with regard to the electric current allowed by the fuse, the electrophoresis apparatus restricts circuit currents only below a relatively high limit value, since the fuse must allow electric currents required for experiments. The prior art thereby requires elaborate care for handling and poses extremely serious problems for practical use.

SUMMARY AND OBJECTS OF THE INVENTION

It is therefore a primary object of the present invention to provide a simplified electrophoresis apparatus which can be operated stably without imposing excessive burdens on users, compactly configured, light weight, and perform electrophoresis as well as conventional apparatus.

For accomplishing this object, the simplified electrophoresis apparatus according to the present invention is configured as an apparatus which comprises a rectifier means for rectifying and delivering an AC current from a universal AC power source, an electrophoresis cell, and an electric controller for applying an electric output from the rectifier circuits to a carrier disposed in the electrophoresis cell. The electric controller comprises control means capable of indirectly controlling a driving section which controls the electric output from the rectifier circuit in accordance with external inputs so as to constitute a safe interface which allows electrophoresis to be carried out as desired with less deterioration of the driving section. The driving-section directly controls the electrophoresis outputs so that the electrophoresis apparatus can be used stably and safely.

The electric controller of the present invention is configured so that the controller cannot be connected or energized when the electrophoresis cell is not protected with a cover. The cover for the electrophoresis cell is configured so as to have a semicylindrical or semispherical surface for preventing water drops from adhering, to an observation surface located on a top surface of the cover. The cover also includes a ventilation structure having ventilation holes. The shape of the cover and the ventilation structure prevent condensation and other liquids from clouding a view through the cover and thus the cover improves observation of the experiment.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
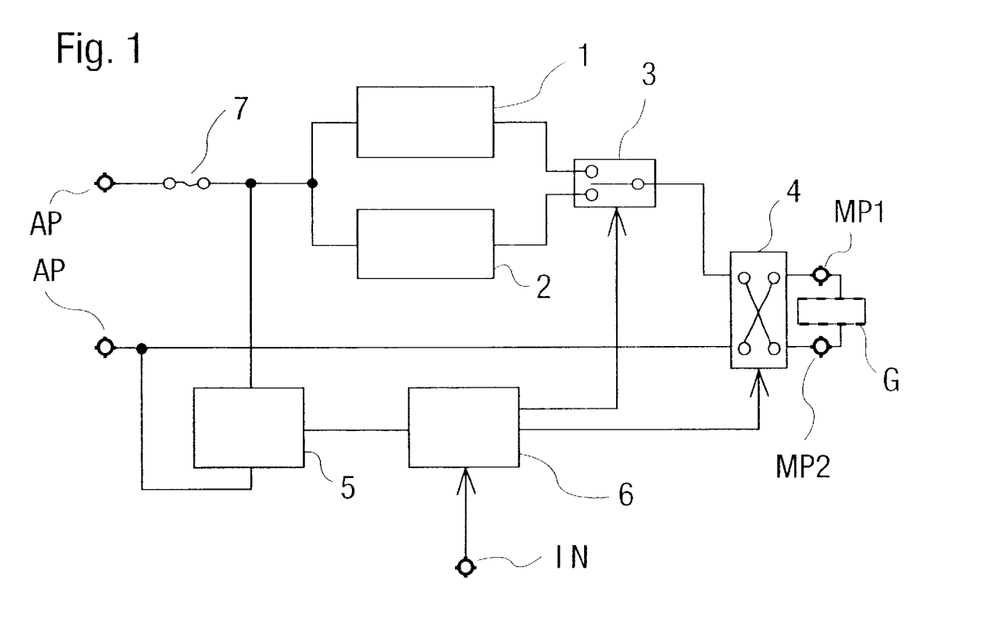
FIG. 1 is a block diagram illustrating an embodiment of the simplified electrophoresis apparatus according to the present invention.

An electric controller according to the present invention will be described with reference to FIG. 1.

The electric controller includes rectifier circuits with a half-wave rectified wave generator 1 and a full-wave rectified wave generator 2 composed of diodes and diode bridges.

These two rectified wave generators are connected to a change-over switch 3 so that the rectified wave generators can be switched by external inputs. The change-over switch 3 is composed, for example, of a relay, an EFT, a transistor or a combination thereof. As a switching element, a relay is preferable since it has a low resistance when it is turned on and high insulating property.

An output of the switch 3 is connected to the polarity switching relay 4 so that it is changed over like the switch 3 according to an external input.

A signal for driving the change-over switch 3 and the polarity switching relay 4 is driven by input means 6 which outputs a switch driving signal corresponding to a manual control activated by control means 5 for outputting a DC voltage converted from a universal AC voltage for driving a low voltage type driving elements such as a low voltage IC and an external input IN such as a signal transmitted by way of a transmitting medium such as radio waves or infrared rays.

A reference numeral 7 represents a fuse which is blown off for protecting the circuits and an operator in occurrence of an overcurrent, etc. A reusable element such as a small circuit breaker may be used on place of the fuse which is not reusable.

In the drawing, a reference symbol AP represents a universal AC connector for AC 100 V to 300 V, and MP1 and MP2 are electric electrophoresis outputs points which are connected to platinum electrodes or the like members. A reference symbol G designates a carrier for electrophoresis such as agarose gel or polyacrylamide gel which is generally used.

The change-over switch 3 can be set in a condition where it connects the half-wave rectified wave generator 1 to the polarity switching relay 4 and the polarity switching relay 4 can be connected so as to set the MP1 and MP2 in the positive direction and in the negative direction respectively.

The AP connectors are connected to a universal AC electric outlet such as a domestic plug socket. A universal AC current is supplied through the fuse 7 to the half-wave rectified wave generator 1, the full-wave rectified wave generator 2 and the control means 5.

Figure 3:
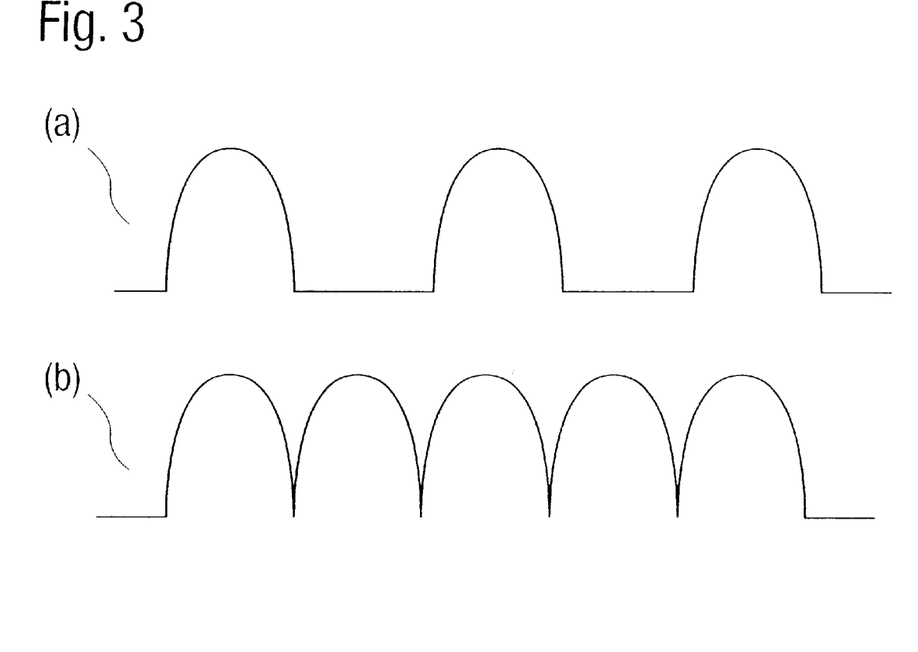
FIG. 3a is a diagram of on type of rectified waveform.
FIG. 3b is a diagram illustrating another type of rectified waveform.

The input universal AC current is converted by the halfwave rectified wave generator 1 into a half-wave rectified wave (FIG. 3a), and supplied through the change-over switch 3 and the polarity switching relay 4 to the electrophoresis output points MP1 and MP2.

Since the change-over switch 3 and the polarity switching relay 4 have very low resistance when turned on, the half-wave rectified wave generated by the half-wave rectified wave generator 1 is efficiently supplied to the electrophoresis output points MP1 and MP2.

When a button switch or a similar member is depressed, an input is generated as the external input IN, and the input means 6 generates a control signal such as a DC pulse on the basis of this input. At the same time, if a control signal is generated and delivered to a switch section selected as a destination, the change-over switch 3 is turned to connect the full-wave rectified wave generator 2 to a polarity switching relay 4 for delivering the full-wave rectified wave (FIG. 3b) to electrophoresis output terminals MP1 and MP2.

When an external input 1 generates an input for changing polarities of the polarity switching relay 4, input means 6 delivers a similar signal to the polarity switching relay 4, thereby providing rectified outputs to set the electrophoresis output points MP2 and MP1 in positive and negative directions respectively.

The electric controller according to the present invention described above provided electrophoresis outputs which are as effective as conventional outputs but operate more safely since the electric controller operates at low voltage levels obtained by controlling the universal AC voltage with the control means 5, etc. The electric controller can also easily permit the connection of timers and other functions. Further, the electric controller can prevent directly manipulated members from deteriorating even when they are manipulated roughly by users, and the electric controller allows the switching section to be controlled safely and stably since the switching section, which directly prepares electrophoresis electric outputs, is kept under indirect electric control.

[First Embodiment]

Figure 2:
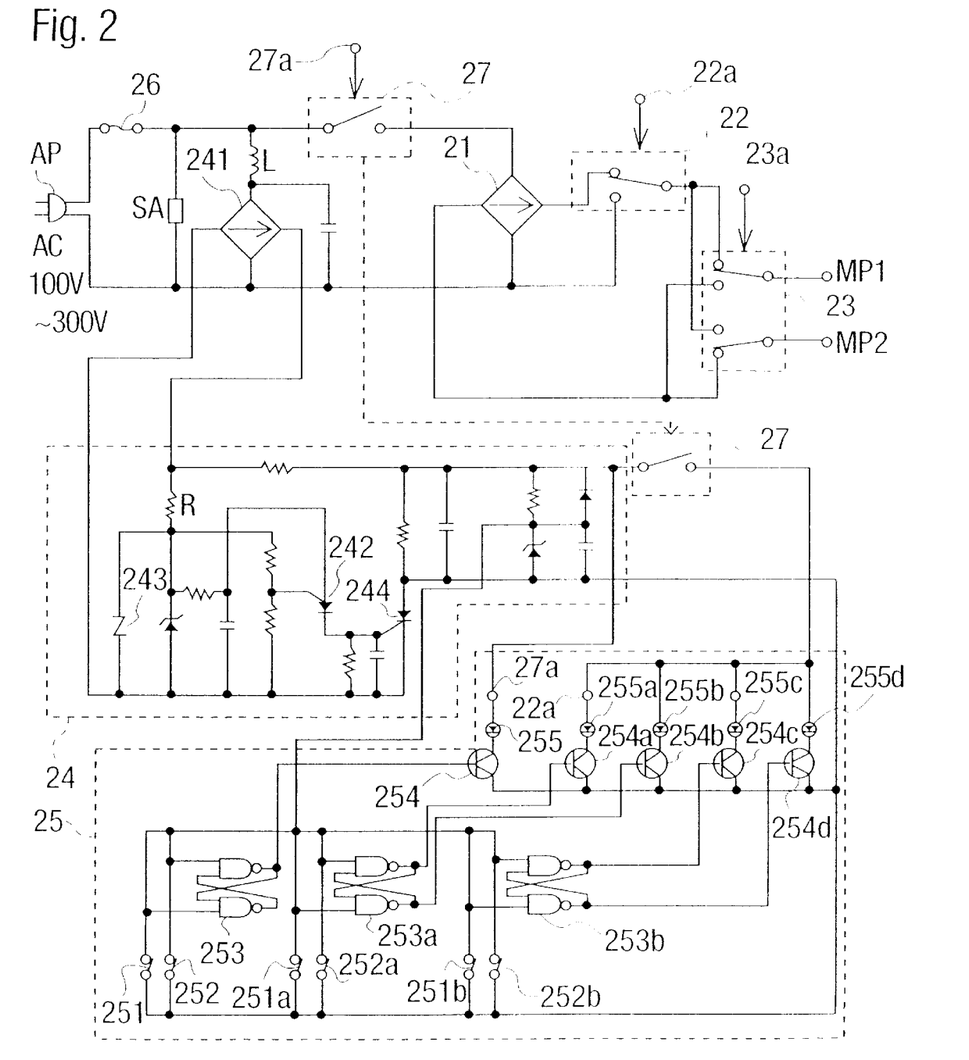
FIG. 2 is a circuit diagram illustrating another embodiment of the simplified electrophoresis apparatus according to the present invention.

Now, a more concrete embodiment will be described with reference to FIG. 2.

Reference numeral 21 represents a rectifier which is composed of a diode bridge and provides a half-wave rectified or full-wave rectified output. A relay 22 performs a switching operation with a signal from an input terminal 22a. A polarity switching relay 23 performs a switching operation with an electric signal from an input terminal 23a. Two output switching relays 27 provide and intercept an output to and from electrophoresis output and input means in accordance with an input fed into an input point 27a.

A control circuit 24 prepares a low DC voltage and comprises a circuit which establishes an electrically shielded condition when an overcurrent or overvoltage is received.

A reference numeral 241 designates a rectifier which has a composition similar to that of the rectifier 21 described above.

A reference numeral PUT 242 denotes a negative resistance element and sidac 243 is also a negative resistance element. A reference numeral 244 represents a thyristor. A reference symbol SA designates a surge absorber which serves for absorbing a counter-electromotive force of an inductor L.

An input means 25 comprises a manual control switch and is used for delivering a signal, which is generated by depressing this switch, to the relays 22, 23 and 27. In this embodiment, 251, 252, 251a, 251b, 252a and 252b are for delivering control signals to the change-over switch 3, and are, for example, membrane-like depressing switches which are electrically connected when depressed and electrically disconnected when released. 253, 253a and 253b are flip-flop circuits which are composed of combinations of NAND circuits.

254, 254a, 254b, 254c and 254d are switching transistors which are turned on and off by outputs from the flip-flop circuits disposed at the preceding stage.

255, 255a, 255b, 255c and 255d are LEDs for displaying circuit operations.

Now, operations of this embodiment will be described below.

The input terminals AP are connected to a universal AC power source of 100 V AC for supplying the universal AC current to the control circuit 24 and the relay 27.

In the control circuit 24, the universal AC current is input into a rectifier 241 and full-wave rectified. PUT 242 operates as a portion of a circuitry like an oscillator circuit which receives a full-wave rectified wave and outputs a trigger pulse to a gate of thyristor 244 at a rising time of the wave. On the basis of the trigger pulse, etc., the thyristor 244 turns on and off for controlling phases of the full-wave rectified wave, thereby lowering a voltage to be supplied to the input means 25. The voltage is lowered, for example, at a ratio of ⅓ to ¼, or to approximately 40 V when an input voltage is 120 V, though it may be lowered at an optional ratio dependently on ratings for parts composing the input means 25.

When output of the flip-flop circuit 253 is set at a low level in the input means 25, the output. Of the flip-flop circuit 253 is set at a high level and the switching transistor 254 is turned on by depressing the switch 251. The LED 255 glows and the current is supplied to a control input point 27a of the relay 27, thereby turning on the relay 27.

The flip-flop circuit 253 is kept in this condition until the switch 252 is depressed. When the switch 252 is depressed, the output of the flip-flop circuit 253 is set at the low level and the LED 255 goes out, thereby turning off the relay 27.

When the relay 27 is turned on, the universal AC current is supplied to the rectifier 21, the rectifier 21 delivers both the full-wave rectified wave and half-wave rectified wave, and the relay 22 switches electric connections between these two outputs and the polarity switching relay 23 with an input to the relay control input point 22a.

Further, the relay 23 functions to switch polarities of the output of the rectifier connected by way of the relay 22 and provide the output to the electrophoresis output terminals MP1 and MP2. First, the relay 23 is connected to provide a rectified output which sets MP1 and MP2 in the positive direction and the negative directions respectively. In this condition, a half-wave rectified output in the positive direction and a half-wave rectified output in the negative direction are provided to the electrophoresis output terminals MP1 and MP2 respectively. In this condition, the, switching transistor 254a of the flip-flop circuit 253a is turned off for providing the output at the low level and the switching transistor 254b is turned on for providing the output at the high level from the opposite side. The LED 255b glows to indicate that the half-wave rectified output is provided.

When the switch 251 a is depressed, the output of the flipflop circuit 253a is inverted to turn on the transistor 254a and glow the LED 255a. On the other hand, the LED 255b goes out and the current is supplied to the relay control input terminal 22a and selected conditions of the relays are switched, whereby the full-wave rectified output is provided to set the electrophoresis output terminals MP1 and MP2 in the positive direction and the negative direction respectively. When the switch 252a is depressed, the output of the flip-flop circuit 253a is inverted once again and the current is not supplied any longer to the relay control input terminal 22a, thereby changing over the relay 22.

The switching transistor 254c for the flip-flop circuit 253b is turned off to provide an output at a low level, the switching transistor 254b is turned on to provide an output at a high level on the opposite side and the LED 255d glows to indicate that the MP1 is providing output in the positive direction.

When the switch 251b is depressed, the output of the flipflop circuit 253b is inverted, the transistor 254c is turned on and the LED 255c glows, whereas the LED 255d goes out, the current is supplied to the relay control input terminal 23a, the polarity selecting condition of the relay 23 is changed over, and the full-wave rectified output is provided to set the electrophoresis output terminals MP1 and MP2 in the negative direction and the positive direction respectively.

When the switch 252a is depressed, the output of the flipflop circuit 253a is inverted once again and the current supply to the relay control terminal 22a is stopped, thereby changing over the relay 22.

Then, description will be made of operations which are performed in occurrence of an overcurrent or an abnormal voltage due to an abnormality. When an overcurrent is supplied to a main circuit around the rectifier 21, the fuse 26 is heated and blown, thereby opening the main circuit and stopping the electrophoresis output.

When an overcurrent or an abnormal voltage is generated due to injury of a resistor R in the control circuit, the thydac 243 is turned on to supply an overcurrent to the fuse 26, thereby opening the circuit.

Since the electric controller described concretely as the embodiment (except the electrophoresis cell) is composed of parts most of which consume small amounts of electric energy and configured as universal chips, it can be assembled so as be accommodated in a housing measuring approximately 40 cm deep by 80 cm wide by 26 corn high, for example, or configured compact and light in weight.

(Second Embodiment)

Figure 4:
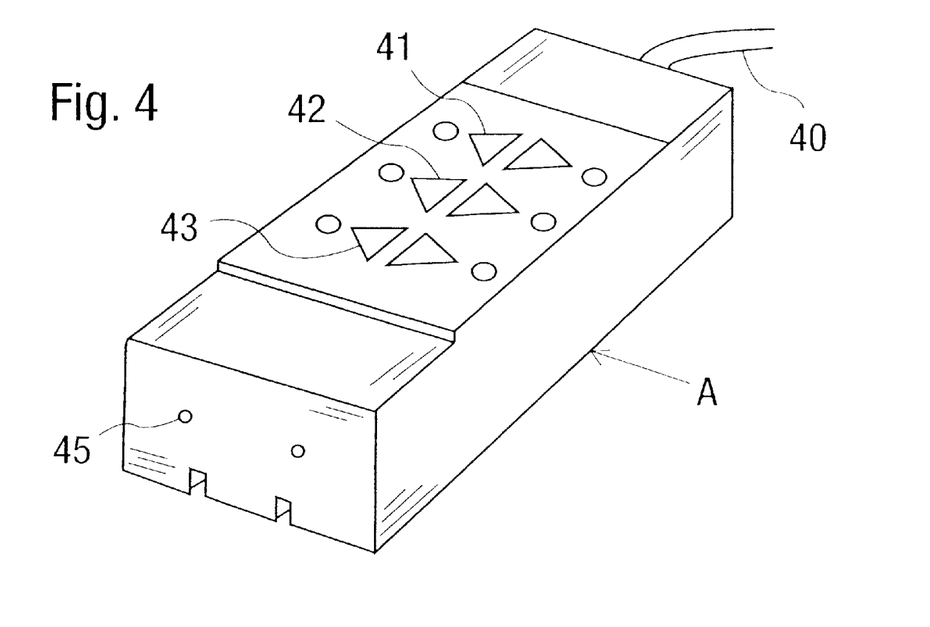
FIG. 4 is a perspective view illustrating an electric controller.
Figure 5:
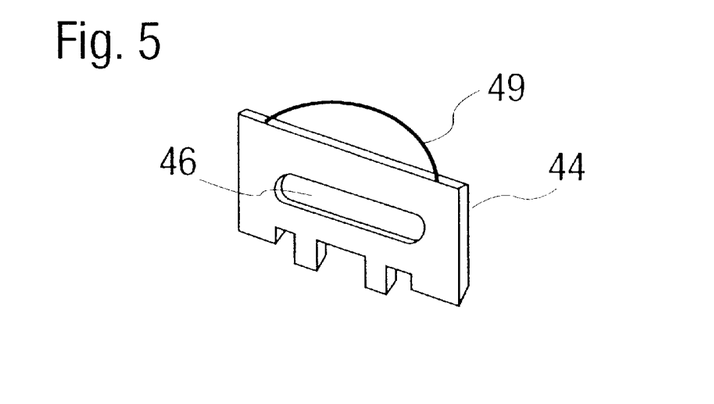
FIG. 5 is a perspective view illustrating a shutter for the electric controller.
Figure 6:
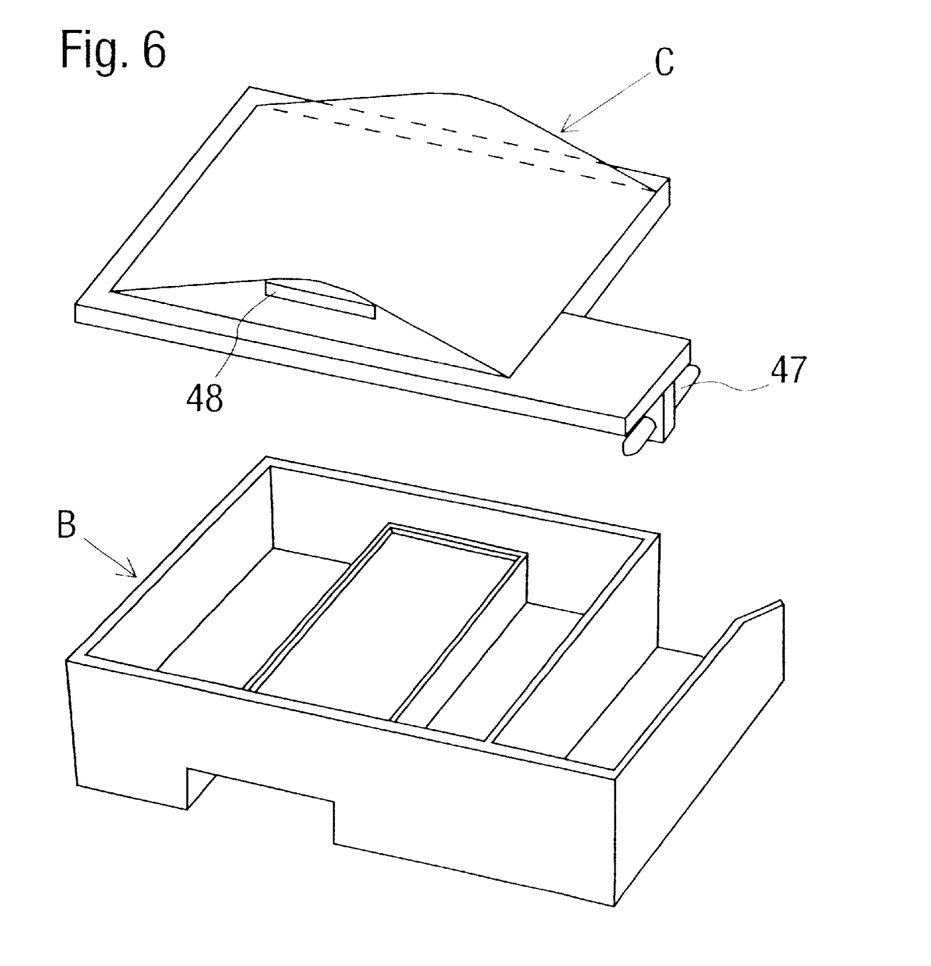
FIG. 6 is a perspective view of the electric controller with the shutter attached.
Figure 7:
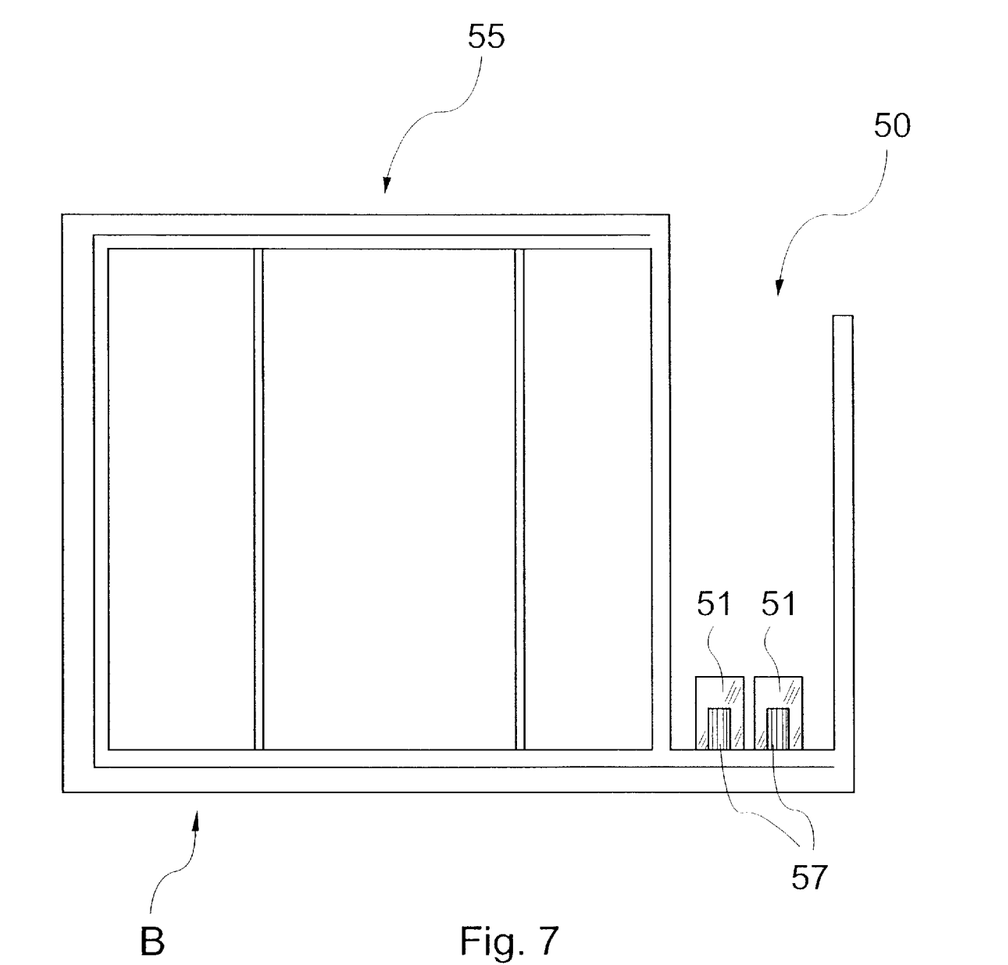
FIG. 7 is a top view of the electrophoresis cell unit.

As shown in FIG. 4, an electric controller A has an input section 40, a polarity switching relay 41, a rectified wave selector switch 42, a power input switch 43 and an output terminal which is configured as a socket 45, and disposed in one end of a housing of the electric controller A. As shown in FIG. 7, an electrophoresis cell unit B has a recess 50 for receiving the electric controller A and a tank portion 55 for holding the electrophoresis gel. The one end of the electric controller having the socket 45 is slid head first into the recess 50. A convex terminal 57 is disposed in the recess 50 of the electrophoresis cell unit B and is inserted into the socket 45 of the controller A when the controller A is fully inserted into the recess 50 for electrically connecting the electric controller A to the electrophoresis cell unit B. The socket 45 of the output terminal is always closed with a shutter 44 when the electric controller A is removed from the recess 50. The shutter 44 is movably arranged on the end of the controller A and the shutter 44 urged downward in the housing of the electric controller A by a spring 49. When the shutter 44 is in the downward or closed position, the socket is closed. The shutter 44 defines a slot 46 which uncovers the socket 45 when the shutter is in the upward or opened position. When the electric controller A is inserted into recess 50 of the electrophoresis cell unit B, the shutter 44 is pushed upwards by convex ribs or ramps 51. This moves the elongated slot 46 in the shutter 44 coincident with the socket 45. The convex rib formed on the electrophoresis cell unit B in a direction of the inserting the electrophoresis cell and the mounting of the shutter 44 on the electric controller A is configured to allow the shutter 44 to be pushed up by this convex rib 51.

Figure 8:
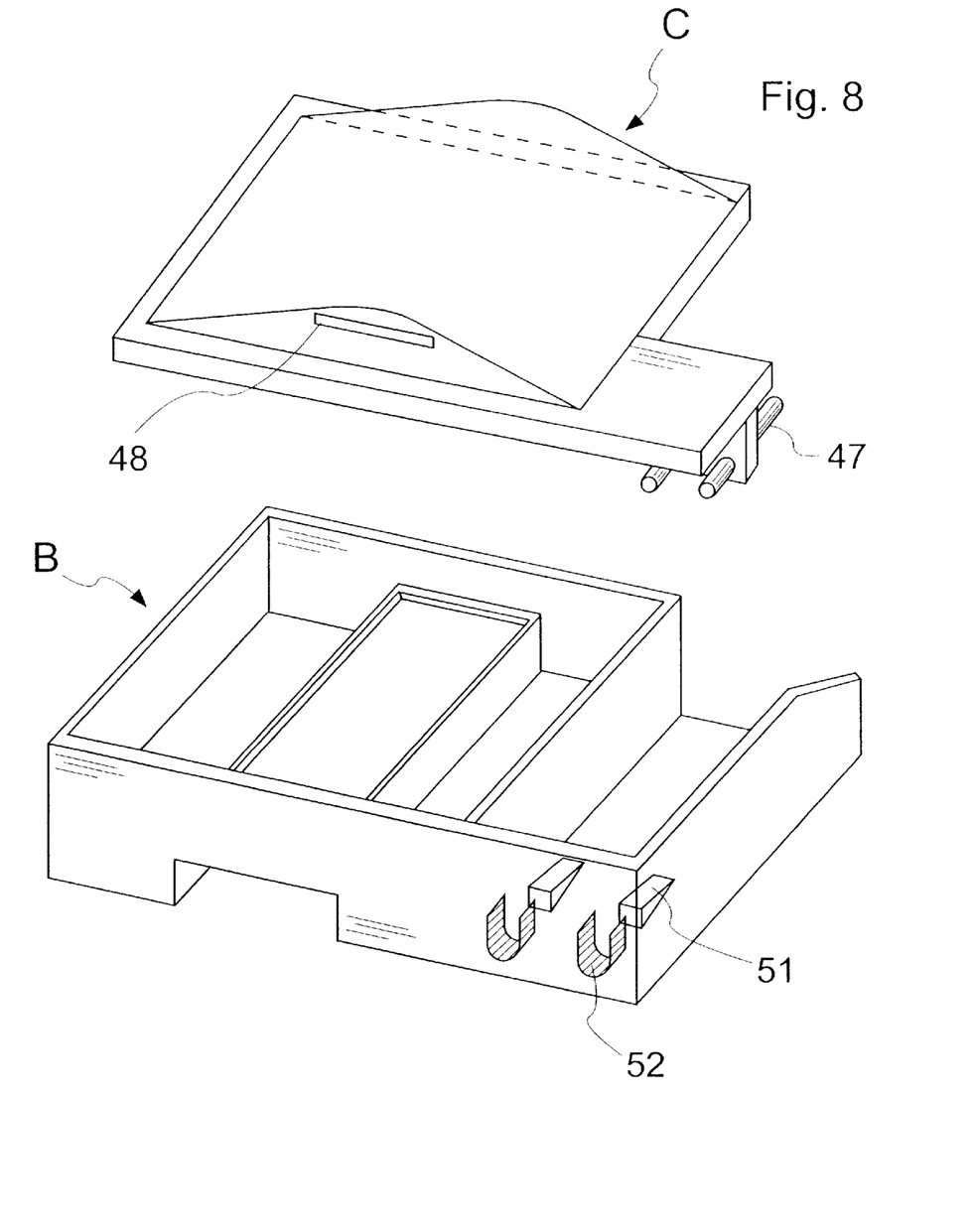
FIG. 8 is a perspective view of a cover and the electrophoresis cell unit.

In a further embodiment, as shown in FIG. 8, the electrophoresis apparatus according to the present invention is configured, for security of use, so as not to allow electrical connection between the electrophoresis cell unit B and the electric controller A so long as the electrophoresis cell unit B is not protected with a cover C.

For composing a security or protective mechanism in this embodiment, a terminal 52 in the recess 50 of the electrophoresis cell unit B is not configured as the convex terminal described above. Instead the electric terminal 52 is configured so as not to be electrically connected to the controller A when the controller A is set in the cell unit B. A convex terminals 47 is formed on electrophoresis cell cover C as a conductive connector between electric terminal 52 and socket 45 of the controller. One end of the convex terminals 47 is plugged into the socket 45 of the electric controller A and the other end of the convex terminals 47 is brought into contact with terminal 52 of the electrophoresis cell unit B for establishing an electrical connection between the two.

Accordingly, an electric current cannot be supplied to the electrophoresis cell unit B whenever the electrophoresis cell B is uncovered by the cover C. Further, the cover C is configured so as to have a semicylindrical or semispherical form, see FIG. 8, so that vapor produced from an electrophoresis liquid which is normally heated to 40 degrees C. can be removed along a slanted surface. Furthermore, a ventilation slot 48 is formed in a side surface and the cover C is engaged with the electrophoresis cell unit B by way of convexities formed at an adequate intervals so as to form air vents or a ventilation structure between these members.. This allows the electrophoresis processes to be observed free from hindrance due to water drops.

INDUSTRIAL APPLICABILITY

As understood from the foregoing description, the present invention makes it possible to obtain an electrophoresis apparatus which is capable of providing excellent electrophoresis outputs, able to be configured compact and light weight since the apparatus can be composed of elements having sizes of several millimeters without requiring any special parts, and operates stably with a safe interface which is constituted by indirectly driving and controlling electrically and mechanically, and a controller for controlling a user's interface and electrophoresis. The control is also very safe since it is performed by control means at low voltages obtained by adjusting a universal AC voltage.

While specific embodiments of the invention have been shown and described in detail to illustrate the application of the principles of the invention, it will be understood that the invention may be embodied otherwise without departing from such principles.

What is claimed is:

1. An electrophoresis apparatus comprising:
   an electric controller with an output terminal shaped as a socket;
   in electrophoresis cell unit positionable adjacent said electric controller, said electrophoresis cell unit including an input terminal;
   a cover positionable over said dectrophoresis cell unit, said cover including a cover terminal, said cover and said cover terminal being shaped to electrically connect said output terminal of said electric controller to said input terminal of said electrophoresis cell unit when said cover covers said electrophoresis cell unit, wherein said output teal of said electric controller and said input terminal of said electrophoresis cell unit have a concave shape.

2. The apparatus in accordance with claim 1, wherein:
   a shape of said input terminal of said electrophoresis cell unit is not directly connectable to said output terminal of said electric controller.

3. The apparatus in accordance with claim 1, wherein:
   said electrophoresis cell unit dies a recess for receiving said electric controller.

4. The apparatus in accordance with claim 3, wherein:
   said electric controller includes a shutter movable between a first and second position, said first position of said shutter covering said output terminal said second position opening said output terminal, said electric controller includes a spring biasing said shutter in said first position;
   said electrophoresis cell unit includes shutter movement means for moving said shutter into said second position when said electric controller is positioned in said recess of said electrophoresis cell unit.

5. The apparatus in accordance with claim 4, wherein:
   said shutter movement means includes a convex rib in said recess of said electrophoresis cell unit.

6. The apparatus in accordance with claim 1, wherein:
   said cover has a curved surface having one of a semi-cylindrical and semi-spherical shape, said cover also defining openings for ventilation of said electrophoresis cell unit.

7. The apparatus in accordance with claim 6, wherein:
   said opening is in a horizontal direction.

8. The apparatus in accordance with claim 7, wherein:
   said electrophoresis cell unit defines a recess for receiving said electric controller;
   said output terminal of said electric controller and said input terminal of said electrophoresis cell unit have a concave shape;
   said electric controller includes a shutter movable between a first and second position, said first position of said shutter covering said output terminal, said second position opening said output terminal, said electric controller includes a spring biasing said shutter in said first position;
   said electrophoresis cell unit includes shutter movement means for moving said shutter into said second position when said electric controller is positioned in said recess of said electrophoresis cell unit,
   said shutter movement means includes a convex rib in said recess of said electrophoresis cell unit,
   said cover has a curved surface having one of a semi cylindrical and semi-spherical shape, said cover also define openings for ventilation of said electrophoresis cell unit, said opening form a horizontal passage.

9. An electrophoresis apparatus comprising:
   an electric controller with an output terminal shaped as a socket and with a built-in electric circuit for converting a commercial AC power source into a rectified electric output for electrophoresis, said electric controller including a shutter movable between a first and second position, said first position of said shutter covering said output terminals said second position opening said output terminal said electric controller including a spring biasing said shutter in said first position;
   an electrophoresis cell unit defining a recess receivable of said electric controller, said electrophoresis cell unit including shutter movement means for moving said shutter into said second position when said electric controller is positioned in said recess of said electrophoresis cell unit, said shutter movement means including a convex rib in said recess of said electrophoresis cell unit;
   a convex input terminal positioned in said recess of said cell unit, said convex input terminal being insertable into said socket of said controller when said controller is inserted into said recess of said cell unit.

10. The apparatus in accordance with claim 9, further comprising:
    a cover positionable over said controller and said cell unit, said cover has a curved surface having one of a semi-cylindrical and semi-spherical shape, said cover also defining openings for ventilation of said electrophoresis cell unit.

11. The apparatus in accordance with claim 10, wherein:
    said opening is in a horizontal direction.

12. The apparatus in accordance with claim 11, wherein:
    said electric controller includes a shutter movable between a first and second position, said first position of said shutter covering said output terminal said second position opening said output terminal, said electric controller includes a spring, biasing said shutter in said first position;
    said electrophoresis cell unit includes shutter movement means for moving said shutter into said second position when said electric controller is positioned in said recess of said electrophoresis cell unit,
    said shutter movement means includes a convex rib in said recess of said electrophoresis cell unit.

13. An electrophoresis apparatus comprising:
    an electric controller with an output terminal shaped as a socket;

an electrophoresis cell unit positionable adjacent said electric controller, said electrophoresis cell unit including an input terminal;

a cover positionable over said electrophoresis cell unit, sad cover including a cover terminal, said cover and said cover terminal being shaped to electrically connect said output terminal of said electric controller to said input terminal of said electrophoresis cell unit when said cover covers said electrophoresis cell unit, wherein a shape of said electric controller, a shape of said electrophoresis cell unit, a shape of said input terminal of said electrophoresis cell unit, and a shape of said output terminal of said electric controller are formed to block said input terminal of said electrophoresis cell unit from being directly connected to said output terminal of said electric controller.

\* \* \* \* \*